United States Patent

Takizawa et al.

[11] Patent Number: 4,596,804
[45] Date of Patent: Jun. 24, 1986

[54] DIBENZ[B,E]OXEPIN COMPOUNDS

[75] Inventors: Hiroshi Takizawa, Tokyo; Yoshimasa Oiji, Shizuoka; Kenji Ohmori, Mishima; Katsuichi Shuto, Shizuoka, all of Japan

[73] Assignee: Kyowa Hakko Kogyo Co., Ltd., Tokyo, Japan

[21] Appl. No.: 625,000

[22] Filed: Jun. 26, 1984

[30] Foreign Application Priority Data

Jun. 29, 1983 [JP] Japan ................................ 58-118009

[51] Int. Cl.$^4$ ................... A61K 31/495; C07D 405/04
[52] U.S. Cl. ................................... 514/253; 514/305; 514/382; 514/450; 544/366; 544/378; 546/134; 548/252; 549/354
[58] Field of Search ................ 544/378, 366; 546/134; 549/354; 514/253, 305, 382, 450; 548/252

[56] References Cited

U.S. PATENT DOCUMENTS

| 3,509,176 | 4/1970 | Winter et al. | 544/378 |
| 4,011,222 | 3/1977 | Gerecke et al. | 544/378 |
| 4,032,525 | 6/1977 | Gerecke et al. | 544/378 |
| 4,144,337 | 3/1979 | Bastian | 544/378 |

Primary Examiner—Glennon H. Hollrah
Assistant Examiner—James H. Turnipseed
Attorney, Agent, or Firm—Antonelli, Terry & Wands

[57] ABSTRACT

A dibenz[b,e]oxepin compound having an antiallergic activity is represented by the following general formula:

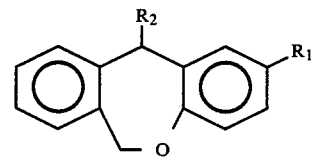

wherein $R_1$ represents a cyano group, a 5-tetrazolyl group, a carbamoyl group or —$CO_2R_3$ wherein $R_3$ represents a hydrogen atom, an alkyl group having 1 to 5 carbon atoms or a 1-(ethoxycarbonyloxy)ethyl group, and $R_2$ represents a 4-alkylpiperazino group wherein the alkyl group has 1 to 5 carbon atoms, a 3-quinuclidinylamino group or —X—$(CH_2)_n$—$NR_4R_5$ wherein X represents —NH—, —S— or —O—, $R_4$ and $R_5$ are same or different and each represents an alkyl group having 1 to 5 carbon atoms and n represents 2 or 3; and the pharmaceutically acceptable acid addition salts or metal salts thereof.

20 Claims, No Drawings

DIBENZ[B,E]OXEPIN COMPOUNDS

This invention relates to dibenz[b,e]oxepin compounds, the pharmaceutically acceptable acid addition salts or metal salts thereof and a pharmaceutical composition containing, as the active ingredient, dibenz[b,e]oxepin compounds. More particularly, the present invention pertains to dibenz[b,e]oxepin compounds of the formula (I):

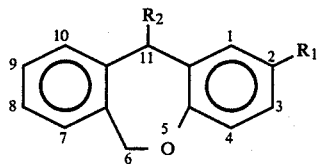

wherein $R_1$ represents a cyano group, a 5-tetrazolyl group, a carbamoyl group or $-CO_2R_3$ wherein $R_3$ represents a hydrogen atom, an alkyl group having 1 to 5 carbon atoms or a 1-(ethoxycarbonyloxy)ethyl group, and $R_2$ represents a 4-alkylpiperazino group wherein the alkyl group has 1 to 5 carbon atoms, a 3-quinuclidinylamino group or $-X-(CH_2)_n-NR_4R_5$ wherein X represents $-NH-$, $-S-$ or $-O-$, $R_4$ and $R_5$ are same or different and each represents an alkyl group having 1 to 5 carbon atoms and n represents 2 or 3; and the pharmaceutically acceptable acid addition salts or metal salts thereof.

In addition, the present invention pertains to a pharmaceutical composition comprising a pharmaceutical carrier and, as an active ingredient, an effective amount of dibenz[b,e]oxepin compounds of the formula (I).

In an effort to meet the constant demand for the development of useful antiallergic agents, the present inventors, have found that dibenz[b,e]oxepin compounds represented by the general formula (I), and the pharmaceutically acceptable acid addition salts and metal salts thereof exhibit an antiallergic activity.

The present invention is described in detail below.

In the definition of $R_3$, $R_4$ and $R_5$ in the general formula (I), the alkyl group having 1 to 5 carbon atoms includes a methyl group, an ethyl group, a propyl group, a butyl group and a pentyl group.

In the definition of $R_2$, the 4-alkylpiperazino group wherein the alkyl group has 1 to 5 carbon atoms includes a 4-methylpiperazino group, a 4-ethylpiperazino group and a 4-propylpiperazino group.

The acid addition salts of the present compound include inorganic acid addition salts such as hydrochloride, sulfate, hydrobromide and phosphate, and organic acid addition salts such as acetate, maleate, fumarate, tartrate, citrate and oxalate. The metal salts include alkali metal salts such as sodium and potassium salts, and alkaline earth metal salts such as magnesium and calcium salts.

The present compounds represented by the general formula (I) can be prepared by the methods shown below.

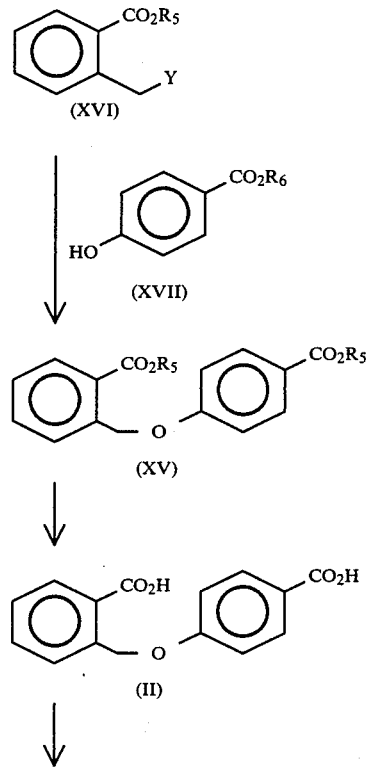

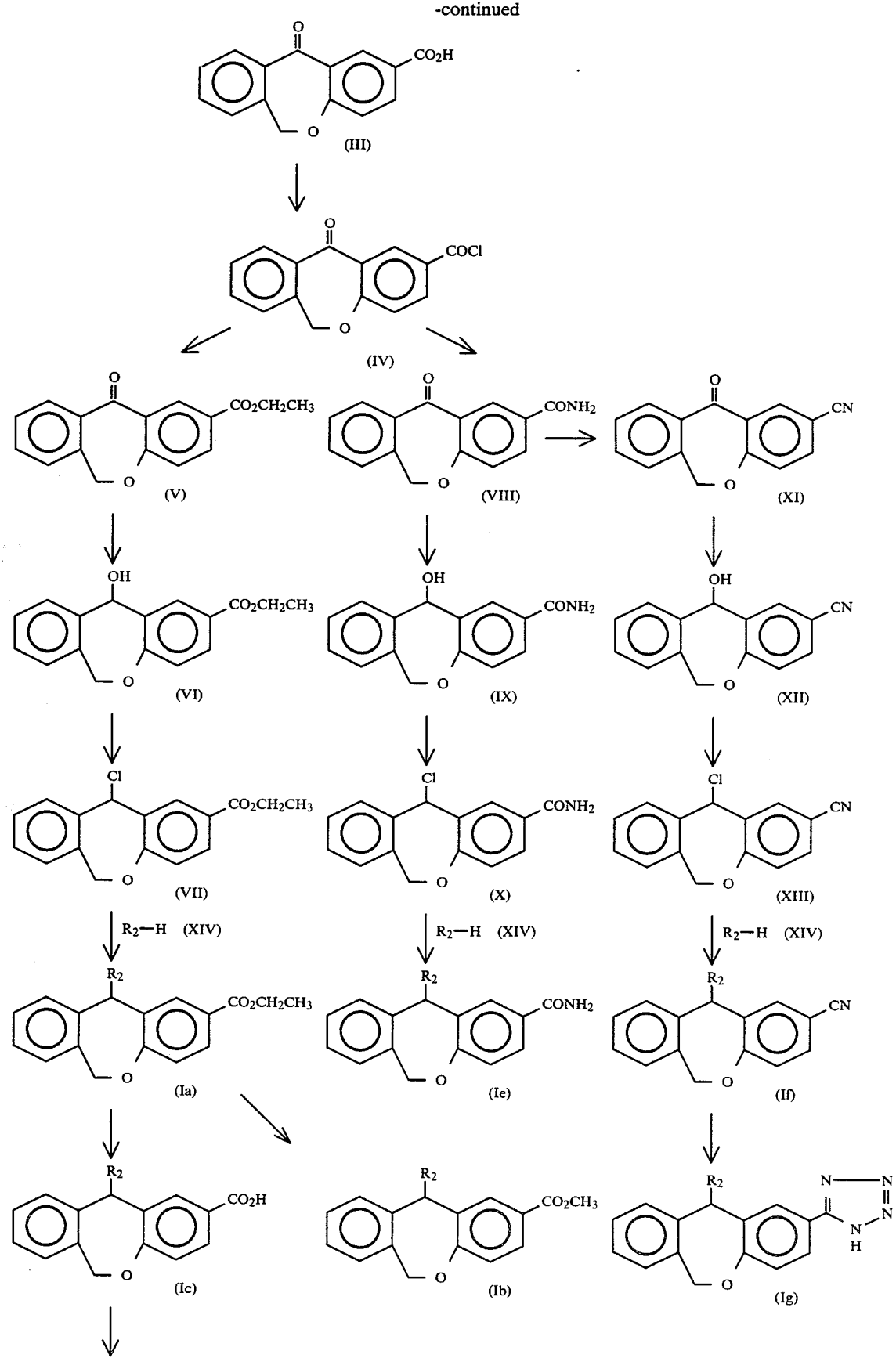

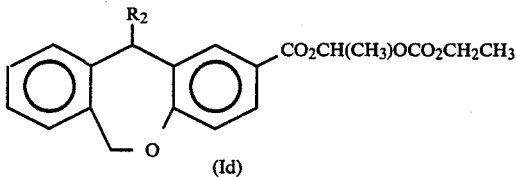

(Id)

In the above formulae, R₂ has the same meaning as defined above, R₅ and R₆ each represent an alkyl group having 1 to 5 carbon atoms and Y represents a halogen atom.

In the definition of R₅ and R₆, the alkyl group having 1 to 5 carbon atoms includes a methyl group, an ethyl group, a propyl group, a butyl group and a pentyl group. The halogen atom represented by Y includes a chlorine atom and a bromine atom.

o-Halomethylbenzoate XVI is allowed to react with an alkali metal salt of p-hydroxybenzoate XVII in an inert solvent, such as N,N-dimethylformamide, at an appropriate temperature from room temperature to 90° C. for 1 to 7 hours to obtain a diester XV. The obtained diester XV is converted to compound II by the reaction with a caustic alkali in aqueous alcohol at an appropriate temperature in the range from room temperature to reflux temperature for 1 to 15 hours.

Compounds II and XV are novel compounds which have not been reported in any literature.

p-Hydroxybenzoate XVII, the starting material, is commercially available as reagents for organic synthesis, and o-halomethylbenzoate XVI is a known compound which can be easily prepared by a known method, for example, by halogenation of the corresponding o-toluate (commercially available) with an N-halosuccinimide [J. Med. Chem., 17, 1020 (1974)].

Synthesis of compound III from compound II is described in detail below.

It was hitherto considered difficult to prepare compound III through direct cyclization of compound II because of the presence of the carboxyl radical, which is a strong electron withdrawing group, at its 2-position. In fact, there is no paper which reports success in such a direct synthesis. The same is the case with the compounds bearing a carboalkoxy, carbamoyl or cyano group, which can be easily converted into a carboxyl group, also because of their strong electron withdrawing influence. This fact may be apparent from Japanese Published Unexamined Patent Application No. 21679/1983 which describes a method of preparing compound III from o-(p-bromophenoxymethyl)benzoic acid. That is, although bromine is electron withdrawing due to its inductive effect, its tautomeric effect serves to suppress the decrease in electron density at the position on the benzene ring subject to electrophilic substitution reaction. This bromo compound was subjected to cyclization by the action of trifluoroacetic anhydride in the presence of boron trifluoride etherate to form 2-bromo-6,11-dihydro-11-oxodibenz[b,e]oxepin, which was then treated with cuprous cyanide in N,N-dimethylformamide under reflux condition to convert the bromo radical into a cyano group, followed by hydrolysis of the resultant cyano group.

In accordance with the present invention, it has been found that compound III can be prepared directly from compound II by heating in sulfolane at 100° to 110° C. for 4 to 5 hours in the presence of polyphosphoric acid, although the yield is 40 to 65%.

The present compound is prepared from compound III obtained as above through the reaction described below.

The carboxylic acid III is heated under reflux with thionyl chloride in an inert solvent such as dichloromethane and toluene for 1 to 5 hours to obtain the corresponding acid chloride IV. Then, compound IV is dissolved in an inert solvent such as toluene, dichloromethane and tetrahydrofuran, and this solution is added to ethanol under cooling with ice or at room temperature, giving the ester V. The corresponding amide VIII is prepared by adding the solution of IV to ammonia water or to a saturated solution of ammonia gas in an inert solvent such as dichloromethane and tetrahydrofuran under cooling with ice or at room temperature. The amide VIII thus obtained can be converted into the nitrile XI by reaction with tosyl chloride in N,N-dimethylformamide in the presence of pyridine at 100° C. for two hours. The ester V, amide VIII and nitrile XI are reduced with sodium borohydride in ethanol, or in a mixed solvent of ethanol with a suitable amount of tetrahydrofuran, under cooling with ice or at room temperature, to give 11-hydroxy compounds VI, IX and XII, respectively. These 11-hydroxy derivatives are reacted with thionyl chloride in an inert solvent such as dichloromethane and diethyl ether under cooling with ice or at room temperature for 1 to 3 hours, yielding 11-chloro compounds VII, X and XIII, respectively.

The 11-chloro derivatives thus obtained are then converted into the desired compounds Ia, Ie and If, respectively, by reaction with 1 to 3 equivalent amount of compound XIV represented by the general formula R₂—H in an inert solvent such as dichloromethane, tetrahydrofuran, N,N-dimethylformamide, diethyl ether and toluene under cooling with ice or at an appropriate temperature lower than the boiling point of the solvent used for 30 minutes to 10 hours, in the presence of a base such as triethylamine and sodium carbonate as required.

Compound Ia is further converted into the corresponding methyl ester Ib through ester exchange by heating in a methanol solution of a caustic alkali under reflux for one hour, and into the corresponding free carboxylic acid Ic through hydrolysis by heating in aqueous methanol solution of a caustic alkali under reflux for 30 minutes to 2 hours. Compound Id can be obtained from compound Ic by reaction of the alkali metal salts with 1.1 to 1.7 equivalent amount of α-chlorodiethyl carbonate in an inert solvent such as N,N-dimethylformamide and tetrahydrofuran with stirring, in the presence of a trace of sodium iodide as required, at an appropriate temperature from 40° to 100° C. for 1 to 5 hours.

Compound Ig can be obtained by reaction of compound If with sodium azide and ammonium chloride in an inert solvent with high dissolving ability, such as N,N-dimethylformamide with stirring at an appropriate temperature from 100° C. to the boiling point of the solvent used for 15 to 25 hours.

The present compound, when obtained as free base (or free acid), may be converted into salt form by the usual method, if desired. When obtained in the form of a salt, they are purified as such.

Typical examples of the present compounds, their structural formulae and physicochemical properties are listed in Tables 1, 2 and 3, respectively.

TABLE 1

| Compound | Name |
|---|---|
| 1 | 11-(4-Methylpiperazino)-6,11-dihydrodibenz[b,e]-oxepin-2-carboxylic acid ethyl ester |
| 2 | 11-(4-Methylpiperazino)-6,11-dihydrodibenz[b,e]-oxepin-2-carboxylic acid methyl ester |
| 3 | 11-(4-Methylpiperazino)-6,11-dihydrodibenz[b,e]-oxepin-2-carboxylic acid diacetate.2H$_2$O |
| 4 | 11-(4-Methylpiperazino)-6,11-dihydrodibenz[b,e]-oxepin-2-carboamide |
| 5 | 11-(4-Methylpiperazino)-6,11-dihydrodibenz[b,e]-oxepin-2-carbonitrile |
| 6 | 11-(4-Methylpiperazino)-2-(5-tetrazolyl)-6,11-dihydrodibenz[b,e]oxepin Na salt |
| 7 | 11-(N,N—dimethylaminoethyl)thio-6,11-dihydro-dibenz[b,e]oxepin-2-carboxylic acid ethyl ester |
| 8 | 11-(N,N—dimethylaminoethyl)thio-6,11-dihydro-dibenz[b,e]oxepin-2-carboxylic acid acetate |
| 9 | 11-(N,N—dimethylaminoethyl)thio-6,11-dihydro-dibenz[b,e]oxepin-2-carboamide |
| 10 | 11-(N,N—dimethylaminoethyl)thio-6,11-dihydro-dibenz[b,e]oxepin-2-carbonitrile |
| 11 | 11-(N,N—dimethylaminoethyl)oxy-6,11-dihydro-dibenz[b,e]oxepin-2-carboxylic acid ethyl ester |
| 12 | 11-(N,N—dimethylaminoethyl)oxy-6,11-dihydro-dibenz[b,e]oxepin-2-carboamide |
| 13 | 11-(N,N—dimethylaminoethyl)amino-6,11-dihydro-dibenz[b,e]oxepin-2-carboxylic acid ethyl ester |
| 14 | 11-(N,N—dimethylaminoethyl)amino-6,11-dihydro-dibenz[b,e]oxepin-2-carboamide |
| 15 | 11-(N,N—diethylaminopropyl)amino-6,11-dihydro-dibenz[b,e]oxepin-2-carboxylic acid ethyl ester |
| 16 | 11-(N,N—diethylaminopropyl)amino-6,11-dihydro-dibenz[b,e]oxepin-2-carboamide |
| 17 | 11-(3-Quinuclidinyl)amino-6,11-dihydrodibenz-[b,e]oxepin-2-carboxylic acid ethyl ester |
| 18 | 11-(3-Quinuclidinyl)amino-6,11-dihydrodibenz-[b,e]oxepin-2-carboamide |
| 19 | 11-(4-Methylpiperazino)-6,11-dihydrodibenz[b,e]-oxepin-2-carboxylic acid (1-ethoxycarbonyloxy)-ethyl ester |
| 20 | 11-(N,N—dimethylaminoethyl)thio-6,11-dihydro-dibenz[b,e]oxepin-2-carboxylic acid (1-ethoxy-carbonyloxy)ethyl ester |
| 21 | 11-(4-Methylpiperazino)-6,11-dihydrodibenz[b,e]-oxepin-2-carboxylic acid dihydrochloride.½H$_2$O |
| 22 | 11-(N,N—dimethylaminoethyl)thio-6,11-dihydro-dibenz[b,e]oxepin-2-carboxylic acid hydrochloride.½H$_2$O |

TABLE 2

[Structure: dibenzoxepin core with R$_2$ at position 11 and R$_1$ on aromatic ring]

| Compound | R$_1$ | R$_2$ |
|---|---|---|
| 1 | —COOC$_2$H$_5$ | —N(piperazine)NCH$_3$ |
| 2 | —COOCH$_3$ | " |
| 3* | —COOH | " |
| 4 | —CONH$_2$ | " |
| 5 | —CN | " |
| 6* | [5-tetrazolyl group] | " |
| 7 | —COOC$_2$H$_5$ | —SCH$_2$CH$_2$N(CH$_3$)$_2$ |
| 8* | —COOH | " |
| 9 | —CONH$_2$ | " |
| 10 | —CN | " |
| 11 | —COOC$_2$H$_5$ | —OCH$_2$CH$_2$N(CH$_3$)$_2$ |
| 12 | —CONH$_2$ | " |
| 13 | —COOC$_2$H$_5$ | —NHCH$_2$CH$_2$N(CH$_3$)$_2$ |
| 14 | —CONH$_2$ | " |
| 15 | —COOC$_2$H$_5$ | —NH(CH$_2$)$_3$N(C$_2$H$_5$)$_2$ |
| 16 | —CONH$_2$ | " |
| 17 | —COOC$_2$H$_5$ | —NH-(3-quinuclidinyl) |
| 18 | —CONH$_2$ | " |
| 19 | —CO$_2$CH(CH$_3$)OCOOC$_2$H$_5$ | —N(piperazine)NCH$_3$ |
| 20 | " | —SCH$_2$CH$_2$N(CH$_3$)$_2$ |
| 21* | —COOH | —N(piperazine)NCH$_3$ |
| 22* | —COOH | —SCH$_2$CH$_2$N(CH$_3$)$_2$ |

Note
*Structural formula: Free base or free acid

TABLE 3

| Compound | 1 | 2 | 3 | 4 | 5 | 6 |
|---|---|---|---|---|---|---|
| IR Spectrum (cm$^{-1}$) | (KBr) Glassy free base 2940, 2800, 1710, 1610, 1245, 1005 (KBr) Dihydrochloride 1710, 1610, 1280, 1245, 1190, 1010 | (KBr) Crystalline free base 2940, 2800, 1710, 1615, 1290, 1250 | (KBr) 1390, 1310, 1250, 1230, 1110, 985 | (KBr) Crystalline free base 2940, 2800, 1660, 1385, 1255, 1140 | (KBr) Powdery free base 2940, 2800, 2220, 1605, 1490, 1235 (KBr) Dihydrochloride 2420, 2230, 1610, 1500, 1250, 1005 | (KBr) 2930, 2800, 1620, 1450, 1255, 1000 (KBr) Free acid monohydrate 2940, 1620, 1450, 1425, 1255, 1230 |
| NMR Spectrum (δ-value, ppm) [Solvent] | [CDCl$_3$] 1.34(t, 3H), 2.19(s, 3H), 2.35(s, 8H), 3.95 (s, 1H), 4.26(q, 2H), 4.71(d, 1H), 6.6–7.9 (m, 8H) | [CDCl$_3$] 2.18(s, 3H), 2.33(s, 8H), 3.83(s, 3H), 3.95(s, 1H), 4.71(d, 1H), 6.6–8.0(m, 8H) | [d$_6$ DMSO] 1.92(s, 6H), 2.18(s, 3H), 2.38(s, 8H), 4.03(s, 1H), 4.78(d, 1H), 5.55(s, 7H), 6.6–8.1(m, 8H) | [d$_6$ DMSO] 2.6–3.2(br, 1H), 3.9 (peak for water), 4.13 (s, 1H), 4.77(d, 1H), 6.6–8.0(m, 10H) | [CDCl$_3$] 2.22(s, 3H), 2.33(s, 8H), 3.86(s, 1H), 4.75 (d, 1H), 6.7–7.5(m, 8H) | [CDCl$_3$ + d$_6$ DMSO] 2.18(s, 3H), 2.34(s, 8H), 3.95(s, 1H), 4.69 (d, 1H), 6.7–8.1(m, 8H) |
| M.P. (°C.) | Dihydrochloride 120–125 (dec) | 162–163 | 225–230 (dec) | 231–233 | Dihydrochloride 134–139 (dec) | Free acid monohydrate 170–175 (dec) |
| Elemental Analysis (C H N) | C$_{22}$H$_{26}$N$_2$O$_3$·2HCl | C$_{21}$H$_{24}$N$_2$O$_3$ | C$_{20}$H$_{22}$N$_2$O$_3$·2CH$_3$COOH·H$_2$O | C$_{20}$H$_{23}$N$_3$O$_2$·2H$_2$O | C$_{20}$H$_{21}$N$_3$O·2HCl | C$_{20}$H$_{22}$N$_6$O·H$_2$O |
| Calc. (%) | 60.14  6.42  6.38 | 71.57  6.86  7.95 | 58.29  6.93  5.66 | 64.32  7.29  11.25 | 61.23  5.91  10.71 | 63.14  6.36  22.09 |
| Found (%) | 59.86  6.71  6.13 | 71.47  6.93  7.78 | 58.32  6.64  5.67 | 64.18  6.99  11.03 | 60.98  5.99  10.83 | 63.09  6.09  21.81 |

| Compound | 7 | 8 | 9 | 10 | 11 | 12 |
|---|---|---|---|---|---|---|
| IR Spectrum (cm$^{-1}$) | (NaCl) Pasty free base 2970, 2770, 1710, 1460, 1250, 1115 (KBr) Monohydrochloride 2930, 2670, 1720, 1610, 1240, 1130 | (KBr) 1610, 1550, 1385, 1250, 1110, 1010 | (KBr) Crystalline free base 1660, 1605, 1380, 1255, 1110, 1005 | (NaCl) Oily free base 2770, 2220, 1605, 1495, 1260, 1005 (KBr) Hydrochloride 2930, 2690, 2220, 1610, 1255, 1010 | (NaCl) Oily free base 2930, 2770, 1710, 1615, 1465, 1250 (KBr) Fumarate (1:1) 1700, 1615, 1410, 1255, 1170, 1000 | (KBr) Powdery free base 2940, 1660, 1390, 1260, 1235, 1005 (KBr) Fumarate (2:1) 1655, 1590, 1410, 1255, 1230, 1000 |
| NMR Spectrum (δ-value, ppm) [Solvent] | [CDCl$_3$] 1.37(t, 3H), 2.15(s, 6H), 2.3–2.9(m, 4H), 4.32(q, 2H), 4.85(d, 1H), 5.04 (s, 1H), 6.45(d, 1H), 6.7–8.0(m, 7H) | [CDCl$_3$] 2.0(br, 3H), 2.3–3.0 (br, 10H), 4.82(d, 1H), 5.07(s, 1H), 6.28(d, 1H), 6.7–8.2(m, 7H), 12.1(br, 2H) | [CDCl$_3$] 2.09(s, 6H), 2.3–2.6(m, 4H), 4.78(d, 1H), 4.97(s, 1H), 6.32(d, 1H), 6.6–7.9(m, 9H) | [CDCl$_3$] 2.15(s, 6H), 2.3–2.9(m, 4H), 4.83(d, 1H), 4.95 (s, 1H), 6.39(d, 1H), 6.7–7.6(m, 7H) | [CDCl$_3$] 1.36(t, 3H), 2.18(s, 6H), 2.49(t, 2H), 3.3–3.7(m, 2H), 4.33(q, 2H), 4.87(d, 1H), 5.16(s, 1H), 6.20(d, 1H), 6.7–8.1(m, 7H) | [CDCl$_3$] 2.14(s, 6H), 2.45(t, 2H), 3.3–3.8(m, 2H), 4.88(d, 1H), 5.17(s, 1H), 6.10(d, 1H), 6.5–8.0(m, 9H) |
| M.P. (°C.) | Monohydrochloride 169–171 | 102–105 | 135–140 | Hydrochloride 194–196 | Fumarate (1:1) 153–158 (dec) | Fumarate (2:1) 190–192 |
| Elemental Analysis (C H N) | C$_{21}$H$_{25}$NO$_3$·HCl | C$_{19}$H$_{21}$NO$_3$S·CH$_3$COOH | C$_{19}$H$_{22}$N$_2$O$_2$S | C$_{19}$H$_{20}$N$_2$OS·HCl | C$_{21}$H$_{25}$NO$_4$·C$_4$H$_4$O$_4$ | C$_{19}$H$_{22}$N$_2$O$_3$·½C$_4$H$_4$O$_4$ |
| Calc. (%) | 61.83  6.42  3.43 | 62.51  6.24  3.47 | 66.64  6.47  8.18 | 63.23  5.86  7.76 | 63.68  6.20  2.97 | 65.61  6.29  7.29 |
| Found (%) | 61.59  6.70  3.70 | 62.32  6.07  3.31 | 66.37  6.25  7.90 | 63.02  6.11  8.01 | 63.39  6.21  2.92 | 65.32  6.34  7.35 |

| Compound | 13 | 14 | 15 | 16 | 17 | 18 |
|---|---|---|---|---|---|---|
| IR Spectrum (cm$^{-1}$) | (NaCl) Oily free base 2930, 2820, 1710, 1610, 1240, 1115 (KBr) Dihydrochloride 1710, 1610, 1290, 1245, 1200, 1020 | (KBr) Crystalline free base 1660, 1390, 1265, 1235, 1115, 1005 | (NaCl) Oily free base 2970, 2800, 1710, 1610, 1250, 1120 (KBr) Dihydrochloride 1710, 1615, 1285, 1245, 1120, 1020 | (NaCl) Pasty free base 2970, 1660, 1605, 1380, 1260, 1005 (KBr) Dihydrochloride 1660, 1610, 1390, 1240, 1110, 1010 | (KBr) Powdery free base 2930, 1710, 1615, 1500, 1245, 1120 (KBr) Dihydrochloride 1710, 1610, 1290, 1245, 1195, 1020 | (NaCl) Oily free base 2930, 1660, 1605, 1385, 1240, 1110 |

TABLE 3-continued

| | | | | | |
|---|---|---|---|---|---|
| NMR Spectrum (δ-value, ppm) [Solvent] | [CDCl₃] 1.35(t, 3H), 2.13(s, 6H), 2.3–2.9(m, 5H), 4.33(q, 2H), 4.63(s, 1H), 4.79(d, 1H), 6.8–8.0(m, 7H) | [CDCl₃ + d₆DMSO] 2.12(s, 6H), 2.2–2.7(m, 5H), 4.63(s, 1H), 4.79 (d, 1H), 6.5–8.0(m, 10H) | [CDCl₃] 0.7–1.8(m, 11H), 2.2–2.8 (m, 9H), 4.32(q, 2H), 4.62(s, 1H), 4.80(d, 1H), 6.6–8.0(m, 8H) | [CDCl₃] 0.7–1.9(m, 8H), 2.1–2.7 (m, 9H), 4.58(s, 1H), 4.78(d, 1H), 6.4–7.9 (m, 10H) | [CDCl₃] 1.1–3.0(m, 16H), 4.32 (q, 2H), 4.73(s, 1H), 4.82(d, 1H), 6.5–8.0(m, 8H) | [CDCl₃] 1.1–3.1(m, 13H), 4.63(s, 1H), 4.82(d, 1H), 6.5–7.9(m, 8H) |
| M.P. (°C.) | Dihydrochloride 177–182 (dec) | 130–135 (dec) | Dihydrochloride 155–160 (dec) | Dihydrochloride 265–270 (dec) | Dihydrochloride 118–121 | — |
| Elemental Analysis (C H N) | C₂₁H₂₆N₂O₃·2HCl | C₁₉H₂₃N₃O₂ | C₂₄H₃₂N₂O₃·2HCl | C₂₂H₂₉N₃O₂·2HCl | C₂₄H₂₈N₂O₃·2HCl | C₂₂H₂₅N₃O₂ |
| Calc. (%) | 59.02 6.60 6.55 | 70.13 7.12 12.91 | 61.40 7.30 5.97 | 60.00 7.09 9.54 | 61.94 6.50 6.02 | 72.70 6.93 11.56 |
| Found (%) | 58.77 6.73 6.28 | 69.85 6.84 12.62 | 61.15 7.44 5.75 | 59.75 7.21 9.26 | 61.69 6.75 5.84 | 72.45 7.01 11.39 |

| Compound | 19 | 20 | 21 | 22 |
|---|---|---|---|---|
| IR Spectrum (cm⁻¹) | (KBr) Powdery free base 2930, 2800, 1750, 1610, 1240, 1070 (KBr) Dihydrochloride 1750, 1610, 1370, 1240, 1070, 1000 | (NaCl) Oily free base 2930, 2770, 1760, 1610, 1240, 1075 | (KBr) 3400, 1610, 1580, 1375, 1230 (KBr) Free base 3400, 1610, 1580, 1380 1230 | (KBr) 3400, 2700, 1700, 1620, 1240, 1200 (KBr) Free base 3400, 1610, 1580, 1375, 1225 |
| NMR Spectrum (δ-value, ppm) [Solvent] | [CDCl₃] 1.30(t, 3H), 1.63(d, 3H), 2.23(s, 3H), 2.38 (s, 8H), 3.47(q, 1H), 3.97(s, 1H), 4.27(q, 2H), 4.75(d, 1H), 6.7–8.0(m, 8H) | [CDCl₃] 1.28(t, 3H), 1.62(d, 3H), 2.15(s, 6H), 2.2–3.0(m, 5H), 4.18(q, 2H), 4.83(d, 1H), 5.00(s, 1H), 6.43(d, 1H), 6.7–8.0(m, 7H) | slightly soluble; not measurable | slightly soluble; not measurable |
| M.P. (°C.) | Dihydrochloride ca. 130 (dec) | (Note) Hydrochloride: Uncrystallizable Fumarate: Hygroscopic M.P. measurement and elemental analysis impossible | 197–200 | 223 (dec) |
| Elemental Analysis (C H N) | C₂₅H₃₀N₂O₆·2HCl | Mass spectrum of free base (70 eV) m/e 459, 413, 355, 326, 239, 223, 194, 165, 104 | C₂₀H₂₄O₃N₂Cl₂·½H₂O | C₁₉H₂₂O₃NSCl·¼H₂O |
| Calc. (%) | 56.93 6.11 5.31 | | 57.77 5.94 6.74 | 58.68 5.96 3.60 |
| Found (%) | 56.65 6.30 5.20 | | 57.79 6.02 6.62 | 58.45 5.73 3.52 |

Test methods for determining antiallergic activity and acute toxicity of the present compounds are described below.

Test on Antiallergic Activity

The 48-hour homologous PCA (passive cutaneous anaphylaxis) test was employed. As test animals, male Wistar strain rats weighing 180 to 220 g were used for preparation of antiserum and those weighing 120 to 140 g for PCA test.

(A) Preparation of rat antiserum to EWA

Rat antiserum to egg white albumin (EWA) was prepared by the method of Stotland Share [Canad. J. Physiol. Pharmacol. 52, 1114 (1974)] as follows. One mg of EWA was mixed with 20 mg of aluminum hydroxide gel and 0.5 ml of pertussis/diphtheria/tetanus mixed vaccine, and the mixture was subcutaneously injected to each rat through the sole in four portions. After 14 days, blood samples were taken from the carotid artery, and the serum was separated and stored at −80° C. The 48-hour homologous PCA titer of this antiserum was 1:32.

(B) 48-hour homologous PCA test in rats

Three rats for each group were employed for 48-hour homologous PCA test. Rats were passively sensitized by injecting intradermally at the two spots on the shaved back 0.05 ml portions of the antiserum which was diluted 8-fold with physiological saline. After 47 hours, test compounds or the solutions thereof (physiological saline solution or CMC solution) were orally administered to the rats, and after one hour, the animals were injected intraveneously to tail vein 0.5 ml/100 g body weight of saline containing 2 mg of EWA, together with 1% Evans blue. Thirty minutes after antigen challenge, the rats were sacrificed by exanguination, and the skin was cut out, followed by the evaluation of the intensity of PCA reaction by expressing the amounts of dye leaked. The amounts of dye leaked from the blue-stained section were measured by the metod of Katayama, et al [Microbiol. Immunol. 22, 89 (1978)] as follows. A portion of the blue-stained section cut out with scissors was placed in a test tube containing 1 ml of 1N KOH solution, and incubated at 37° C. for 24 hours. 9 ml of a mixture of 0.6N phosphoric acid and acetone (5:13) was added, and the mixture was shaken and subjected to centrifugation at 2500 rpm for 10 minutes. Then, the absorbance of the supernatant liquid at 620 m$\mu$ was measured, and the amount of eluted dye was determined by using a calibration curve previously prepared. The average of the measurements for the two positions was taken as the value for each individual, and the inhibition rate for each rat was calculated from the following formula:

Inhibition Rate (%) =

$$\frac{\text{(Average Eluted Dye in Control Group)} - \text{(Average Eluted Dye in Test Group)}}{\text{(Average Eluted Dye in Control Group)}} \times 100$$

PCA inhibiting activity was evaluated as positive when the inhibition rate was 50% or higher, and the minimum dose required to achieve positive result for at least one among the three rats in each group was taken as the minimum effective dose (MED). The results of test are shown in Table 4.

Test on Acute Toxicity

The present compound was administered orally (p.o. 300 mg/kg) or intraperitoneally (i.p. 100 mg/kg) to several groups of male dd strain mice weighing 19 to 21 g (each group consisting of three mice), and MLD (minimum lethal dose) was determined by observing the mortality seven days after administration. The results are shown in Table 4.

TABLE 4

| Compound | Acute Toxicity (MLD) mg/Kg | | Antiallergic Activity Number of Positive Rats (among three in each group) Dose | | | | MED mg/Kg |
|---|---|---|---|---|---|---|---|
| | PO | ip | 50 | 10 | 1 | 0.1 | |
| 3 | >300 | >100 | 3 | 3 | 1 | 0 | 1 |
| 4 | >300 | >100 | 3 | 1 | — | — | 10 |
| 6 | >300 | >100 | 1 | 1 | 0 | 0 | 10 |
| 7 | >300 | >100 | 3 | 1 | — | — | 10 |
| 8 | >300 | >100 | 1 | 1 | 0 | 0 | 10 |
| 10 | >300 | >100 | — | 3 | 2 | 0 | 1 |
| 11 | >300 | >100 | 2 | 3 | 1 | 0 | 1 |
| 14 | 300 | >100 | 3 | 2 | 1 | 0 | 1 |
| 17 | >300 | >100 | 3 | 3 | 2 | 1 | 0.1 |
| 19 | >300 | >100 | 3 | 1 | 2 | 0 | 1 |
| 20 | >300 | >100 | 3 | 3 | 3 | 1 | 0.1 |
| 21 | >300 | >100 | — | 2 | 1 | 0 | 1 |
| 22 | >300 | >100 | — | 3 | 3 | 1 | 0.1 |

As is apparent from Table 4, the compounds represented by the general formula (I) have an antiallergic activity and are useful for the treatment of asthma and other allergic diseases.

In view of the pharmacological activity, the compounds represented by the general formula (I) may be used in various pharmaceutical forms for administration. Pharmaceutical compositions of the present invention are prepared by uniformly mixing an effective amount of the compound as the active ingredient, in free form or as an acid addition salt, with a pharmaceutically acceptable carrier.

The carrier may take various forms depending on the pharmaceutical form suitable for administration. It is preferable that the pharmaceutical composition is in single administration form suitable for administration orally or by injection.

To prepare the compositions of the present invention for oral administration, any useful pharmaceutical carrier may be used. For example, oral liquid preparations such as suspensions and syrups can be prepared using water, sugar (e.g. sucrose, sorbitol and fructose), glycols (e.g. polyethyleneglycol and propyleneglycol), oils (e.g. sesame oil, olive oil and soybean oil), antiseptics (e.g. an alkyl parahydroxybenzoate), flavours (e.g. strawberry flavour and peppermint), and the like. Powders, pills, capsules and tablets can be prepared using excipients (e.g. lactose, glucose, sucrose and mannitol), disintegrators (e.g. starch and sodium alginate), lubricants (e.g. magnesium stearate and talc), binders (e.g. polyvinyl alcohol, hydroxypropylcellulose and gelatin), surfactants (e.g. fatty acid ester), plasticizers (e.g. glycerin), and the like.

Tablets and capsules are the most useful single oral administration forms because of the ease of administration. To make tablets and capsules, solid pharmaceutical carriers are used.

An injection solution can be prepared using a carrier comprising salt solution, glucose solution, or a mixture of salt solution and glucose solution.

Although the amount of the active ingredient can be varied over a rather wide range, 1-20 mg/kg/day in one dose or several divided doses is generally considered to be effective.

Certain specific embodiments of the invention are illustrated by the following representative examples.

EXAMPLE 1

In this example, 3.15 g of chloro-oxepincarboxylic acid ethyl ester VII prepared in Reference Example 1 described below and 2.1 g of N-methylpiperazine were dissolved in 50 ml of anhydrous dichloromethane, and the solution was stirred at room temperature for three hours. After concentration of the reaction mixture under reduced pressure, the residue was dissolved in dilute hydrochloric acid. The acidic solution was washed with ether, then made alkaline, and extracted with ether. The ether layer was dehydrated and concentrated under reduced pressure to obtain 2.57 g of 11-(4-methylpiperazino)-6,11-dihydrodibenz[b,e]oxepin-2-carboxylic acid ethyl ester (compound 1) as glassy solid (yield: 67.4%).

This product was dissolved in dichloromethane and then hydrogen chloride gas was blown thereinto. The reaction mixture was concentrated to dryness. Trituration of the residue thus obtained with ether gave dihydrochloride of compound 1.

REFERENCE EXAMPLE 1

In this reference example, 86.64 g of ethyl p-hydroxybenzoate was dissolved in 725 ml of anhydrous N,N-dimethylformamide, and 20.86 g of sodium hydride (60% dispersion in oil) was added thereto under ice-cooling. After stopping of effervescence, 126.75 g of ethyl o-bromomethylbenzoate was added thereto and the mixture was stirred at room temperature for two hours. Then, the reaction mixture was poured into 3.5 liters of cold water, and the crystals separated out were collected by filtration. The crystals thus obtained were heated in a mixture of 200 ml of methanol, 200 ml of water and 150 ml of 10N aqueous NaOH solution under reflux for one hour. Methanol was distilled away under reduced pressure and 2 liters of water was added. The resultant aqueous solution was washed with 500 ml of ether, and the pH was adjusted to 1.5. The crystals separated out were collected by filtration and dried to obtain 119.0 g of 2-(4-carboxy)phenoxymethylbenzoic acid II (yield: 83.8%). IR spectrum (KBr tablet, cm$^{-1}$): 1680, 1610, 1415, 1245, 1170, 1030.

Next, 14.90 g of the dicarboxylic acid II was dissolved in 150 ml of sulfolane. Then, 150 ml of polyphosphoric acid was added thereto with stirring under heating at 100° to 110° C. while flowing nitrogen gas. Heating with stirring was continued for one hour, the reaction mixture was poured into 750 ml of ice-cold water, and the crystals separated out were collected by filtration. The crystals thus obtained were then heated in a mixture of 100 ml of methanol, 100 ml of water and 25 ml of 10N aqueous NaOH solution under reflux for 2.5 hours. Methanol was distilled away under reduced pressure, and 200 ml of water was added. The resultant aqueous solution was washed with 100 ml of ether, and the pH was adjusted to 1.3. The crystals separated out were collected by filtration and dried, yielding 8.75 g of 6,11-dihydro-11-oxodibenz[b,e]oxepin-2-carboxylic acid III (yield: 62.9%). Recrystallization from ethyl acetate gave pure crystals having a melting point of 250°-252° C. IR spectrum (KBr tablet, cm$^{-1}$): 1690, 1650, 1610, 1410, 1295, 1130.

Next, 30.44 g of oxepincarboxylic acid III obtained above was allowed to react with 30 ml of thionyl chloride in 200 ml of toluene by heating under reflux for one hour. Concentration of the reaction mixture to dryness under reduced pressure gave 6,11-dihydro-11-oxodibenz[b,e]oxepin-2-carboxylic acid chloride IV in a quantitative yield. One half of this acid chloride IV was added to 300 ml of ethanol, and the mixture was stirred at room temperature for three hours and concentrated under reduced pressure. The residue was dissolved in chloroform, and the solution was washed with a saturated aqueous solution of sodium bicarbonate, dehydrated and concentrated to dryness to obtain 6,11-dihydro-11-oxodibenz[b,e]oxepin-2-carboxylic acid ethyl ester V in a quantitative yield. Recrystallization from n-hexane gave pure crystals having a melting point of 104°-105° C. IR spectrum (KBr tablet, cm$^{-1}$): 2980, 1710, 1650, 1610, 1250, 1010.

The remaining half of the acid chloride IV was added to a mixture of 150 ml of concentrated ammonia and 150 ml of tetrahydrofuran. Then, the mixture was stirred at room temperature for three hours and concentrated under reduced pressure. The residue was vigorously stirred together with 300 ml of saturated aqueous solution of sodium bicarbonate and 100 ml of ether, and the solid was collected by filtration and dried to obtain 6,11-dihydro-11-oxodibenz[b,e]oxepin-2-carboamide VIII in a quantitative yield. Recrystallization from methanol gave pure crystals having a melting point of 227°-228° C. IR spectrum (KBr tablet, cm$^{-1}$): 3430, 3150, 1680, 1635, 1600, 1370.

Then, 25.33 g of oxepin-carboamide VIII obtained above, 28.5 g of tosyl chloride and 30 ml of pyridine were dissolved in 200 ml of N,N-dimethylformamide. The mixture was heated at 100° C. for two hours with stirring and poured into 1 liter of ice-cold water. The resultant mixture was extracted with chloroform, and the chloroform solution was dehydrated and concentrated to dryness to obtain 19.29 g of 6,11-dihydro-11-oxodibenz[b,e]oxepin-2-carbonitrile XI (yield: 82.0%). IR spectrum (KBr tablet, cm$^{-1}$): 2230, 1660, 1605, 1490, 1300, 1140.

Then, 5.91 g of oxepin-carboxylic acid ethyl ester V was dissolved in 70 ml of ethanol. 0.6 g of sodium borohydride was added thereto, and the mixture was stirred at room temperature for three hours and then allowed to stand at room temperature overnight. The reaction mixture was concentrated under reduced pressure and water was added to the residue. The resultant mixture was extracted with dichloromethane, and the organic layer was dehydrated and concentrated to dryness to obtain 5.64 g of 6,11-dihydro-11-hydroxydibenz[b,e]oxepin-2-carboxylic acid ethyl ester VI (yield: 94.7%). Recrystallization from toluene gave pure crystals having a melting point of 104°-106° C. IR spectrum (KBr tablet, cm$^{-1}$): 2920, 1675, 1610, 1290, 1240, 1170; NMR spectrum (CDCl$_3$, δ-value ppm): 1.29(t, 3H), 3.91(s, 1H), 4.23(q, 2H), 4.89(d, 1H), 5.58(s, 1H), 5.90(d, 1H), 6.7-8.0(m, 7H).

In a similar manner as above, 6,11-dihydro-11-hydroxydibenz[b,e]oxepin-2-carboamide IX was prepared from the oxepin-carboamide VIII in a quantitative yield. Recrystallization from tetrahydrofuran gave pure crystals having a melting point of 257°-258° C. IR spectrum (KBr tablet, cm$^{-1}$): 3350, 3180, 1665, 1625, 1410, 1255; NMR spectrum (CDCl$_3$+d$_6$DMSO, δ- value, ppm): 5.10(d, 1H), 5.78, 5.85, 6.09 (each d, total 3H), 6.6–8.1(m, 9H).

In a similar manner as above, 6,11-dihydro-11-hydroxydibenz[b,e]oxepin-2-carbonitrile XII was prepared from the oxepin-carbonitrile XI in a quantitative yield. IR spectrum (KBr tablet, cm$^{-1}$): 2230, 1610, 1500, 1260, 1240, 1000; NMR spectrum (CDCl$_3$+d$_6$DMSO, δ-value, ppm): 5.23(d, 1H), 5.72(d, 1H), 5.88(d, 1H), 6.15(d, 1H), 6.7–7.9(m, 7H).

Then, 5.64 g of ethoxycarbonyloxepinol VI was dissolved in 70 ml of dichloromethane, 3 ml of thionyl chloride was added thereto, and the mixture was stirred at room temperature for one hour and concentrated under reduced pressure to obtain 6,11-dihydro-11-chlorodibenz[b,e]oxepin-2-carboxylic acid ethyl ethyl ester VII in a quantitative yield. IR spectrum (NaCl cell, cm$^{-1}$): 2980, 1710, 1610, 1500, 1250, 1120.

In a similar manner as above, 6,11-dihydro-11-chlorodibenz[b,e]oxepin-2-carboamide X was quantitatively prepared from 5.58 g of carbamoyloxepinol IX. IR spectrum (KBr tablet, cm$^{-1}$): 1660, 1610, 1490, 1260, 1120, 1000.

In a similar manner as above, 6,11-dihydro-11-chlorodibenz[b,e]oxepin-2-carbonitrile XIII was obtained from 11.17 g of cyano-oxepinol XII in a quantitative yield. IR spectrum (KBr tablet, cm$^{-1}$): 2220, 1610, 1495, 1260, 1235, 1000.

EXAMPLES 2–11

The present compounds listed in Table 5 were prepared in a similar manner as in Example 1, except that materials shown in the table were used.

TABLE 5

| | Material | | | | Desired Compound | | |
|---|---|---|---|---|---|---|---|
| Example | Chloro deriv.* | Amount (g) | R$_2$—H (XIV) | Amount (g) | No. | Amount (g) | Yield (%) |
| 2 | Compound X | 2.49 | N—methyl-piperazine | 2.00 | 4 | 1.15 | 37.5 |
| 3 | Compound VII | 4.62 | N,N—dimethyl-aminoethanol | 2.76 | 11 | 2.88 | 53.1 |
| 4 | Compound X | 4.59 | N,N—dimethyl-aminoethanol | 3.00 | 12 | 1.63 | 29.8 |
| 5 | Compound VII | 4.62 | N,N—dimethyl-ethylenediamine | 2.73 | 13 | 1.27 | 23.5 |
| 6 | Compound X | 4.59 | N,N—dimethyl-ethylenediamine | 2.96 | 14 | 1.96 | 35.9 |
| 7 | Compound VII | 4.62 | N,N—diethyl-propanediamine | 4.04 | 15 | 3.11 | 51.4 |
| 8 | Compound X | 4.59 | N,N—diethyl-propanediamine | 4.36 | 16 | 2.12 | 34.4 |
| 9 | Compound VII | 4.62 | 3-Aminoquinuclidine | 3.91 | 17 | 2.14 | 35.8 |
| 10 | Compound X | 4.59 | 3-Aminoquinuclidine | 4.23 | 18 | 0.50 | 8.2 |
| 11 | Compound XIII | 2.56 | N—methyl-piperazine | 2.00 | 5 | 2.65 | 83.1 |

Note *Compounds obtained in Reference Example 1

EXAMPLE 12

A mixture of 3.03 g of chloro-oxepincarboxylic acid ethyl ester VII and 1.42 g of N,N-dimethylaminoethanethiol hydrochloride in 30 ml of anhydrous dichloromethane and 30 ml of N,N-dimethylformamide was heated under reflux for 12 hours. Then, the solvents were distilled off from the reaction mixture under reduced pressure. The residue was dissolved in water and then the aqueous solution was washed with ether. The pH of the aqueous layer was adjusted to 10.0 and the resultant alkaline solution was extracted with ether. The ether layer was dehydrated and concentrated to dryness to obtain 2.91 g of 11-(N,N-dimethylaminoethyl)thio-6,11-dihydrodibenz[b,e]oxepin-2-carboxylic acid ethyl ester (compound 7) (yield: 78.4%).

This compound was dissolved in dichloromethane and then, hydrogen chloride gas was blown thereinto. The reaction mixture was concentrated to dryness, and the residue was triturated in ether to obtain hydrochloride of compound 7.

EXAMPLES 13 AND 14

The compounds listed in Table 6 were prepared in a similar manner as in Example 12 except that materials shown in the table were used.

TABLE 6

| | Material | | | | Desired compound | | |
|---|---|---|---|---|---|---|---|
| Example | Chloro deriv. | Amount (g) | Name | Amount (g) | No. | Amount (g) | Yield (%) |
| 13 | Compound X | 2.74 | N,N—dimethyl-aminoethane-thiol hydrochloride | 1.42 | 9 | 2.89 | 84.5 |
| 14 | Compound XIII | 5.11 | N,N—dimethyl-aminoethane-thiol hydro- | 2.83 | 10 | 5.75 | 88.6 |

TABLE 6-continued

| | Material | | | Desired compound | | |
|---|---|---|---|---|---|---|
| Example | Chloro deriv. | Amount (g) | Name | Amount (g) | No. | Amount (g) | Yield (%) |
| | | | chloride | | | | |

EXAMPLE 15

A mixture of 5.19 g of 11-(4-methylpiperazino)-6,11-dihydrodibenz[b,e]oxepin-2-carboxylic acid ethyl ester (compound 1) and 0.57 g of sodium hydroxide in 90 ml of methanol was heated under reflux for one hour. The reaction mixture was concentrated under reduced pressure to about 20 ml, and the crystals separated out after cooling were collected by filtration to obtain 3.35 g of 11-(4-methylpiperazino)-6,11-dihydrodibenz[b,e]oxepin-2-carboxylic acid methyl ester (compound 2) (yield: 67.1%).

EXAMPLE 16

A mixture of 3.66 g of 11-(4-methylpiperazino)-6,11-dihydrodibenz[b,e]oxepin-2-carboxylic acid ethyl ester (compound 1) and 0.44 g of sodium hydroxide in 100 ml of 50% aqueous methanol was heated under reflux for one hour. The reaction mixture was concentrated to dryness to obtain 11-(4-methylpiperazino)-6,11-dihydrodibenz[b,e]oxepin-2-carboxylic acid sodium salt as residue. This product was subjected to column chromatography on silica gel using methanol:acetic acid (100:3 v/v) as eluent. Then, the main fraction was concentrated to dryness, and the residue was triturated in dichloromethane to obtain 4.10 g of 11-(4-methylpiperazino)-6,11-dihydrodibenz[b,e]oxepin-2-carboxylic acid diacetate/dihydrate (compound 3) (yield: 83.0%)

EXAMPLE 17

In a similar manner as in Example 16, 3.12 g (yield: 77.4%) of 11-(N,N-dimethylaminoethyl)thio-6,11-dihydrodibenz[b,e]oxepin-2-carboxylic acid acetate (compound 8) was prepared by using 3.71 g of 11-(N,N-dimethylaminoethyl)thio-6,11-dihydrodibenz[b,e]oxepin-2-carboxylic acid ethyl ester (compound 7) in place of compound 1.

EXAMPLE 18

In this example, 2.50 g of 11-(4-methylpiperazino)-6,11-dihydrodibenz[b,e]oxepin-2-carboxylic acid sodium salt, which was obtained as intermediate in Example 16, was suspended in 30 ml of anhydrous N,N-dimethyl-formamide and then 2.0 g of α-chlorodiethyl carbonate was added thereto. The mixture was heated at 80° C. with stirring for three hours. The reaction mixture was poured into cold dilute hydrochloric acid and washed with ether. The aqueous layer was extracted with ether after the pH was adjusted to 11.0. Then, the ether layer was dehydrated and concentrated to dryness to obtain 1.44 g of 11-(4-methylpiperazino)-6,11-dihydrodibenz[b,e]oxepin-2-carboxylic acid (1-ethoxycarbonyloxy)ethyl ester (compound 19) (yield: 45.6%) as a powder.

This product was dissolved in dichloromethane and then hydrogen chloride gas was blown thereinto. The reaction mixture was concentrated to dryness, and the residue was triturated in ether to obtain dihydrochloride of compound 19.

EXAMPLE 19

In a similar manner as in Example 18, 2.50 g (yield: 50.9%) of 11-(N,N-dimethylaminoethyl)thio-6,11-dihydrodibenz[b,e]oxepin-2-carboxylic acid (1-ethoxycarbonyloxy)ethyl ester (compound 20) was prepared by using 3.90 g of 11-(N,N-dimethylaminoethyl)thio-6,11-dihydrodibenz[b,e]oxepin-2-carboxylic acid sodium salt, in place of 11-(4-methylpiperazino)-6,11-dihydrodibenz[b,e]oxepin-2-carboxylic acid sodium salt.

EXAMPLE 20

A mixture of 4.35 g of 11-(4-methylpiperazino)-6,11-dihydrodibenz[b,e]oxepin-2-carbonitrile (compound 5), 1.06 g of sodium azide and 0.95 g of ammonium chloride in 30 ml of anhydrous N,N-dimethylformamide was heated at 140° C. with stirring for 20 hours. Then, the reaction mixture was poured into 150 ml of ice-cold water, and washed with ether after the pH was adjusted to 13.5. The aqueous solution was subjected to salting-out process and allowed to stand overnight under cooling. The separated crystals were collected by filtration to obtain 3.02 g of 11-(4-methylpiperazino)-2-(5-tetrazolyl)-6,11-dihydrodibenz[b,e]oxepin sodium salt (compound 6) (yield: 57.7%).

This product was dissolved in dichloromethane, hydrogen chloride gas was blown thereinto, and the reaction mixture was concentrated to dryness. The residue was desalted by treatment with a high-porous type ion-exchange resin, followed by recrystallization from tetrahydrofuran, whereby monohydrate was obtained as crystals.

EXAMPLE 21

Preparation of tablet

A tablet comprising the following components was prepared in a conventional manner.

Component 11-(4-Methylpiperazino)-6,11-dihydrodibenz[b,e]oxepin-2-carboxylic acid diacetate.$2H_2O$ (compound 3): 30 mg
Lactose: 60 mg
Potato starch: 30 mg
Polyvinyl alcohol: 2 mg
Magnesium stearate: 1 mg
Tar pigment: q.s.

EXAMPLE 22

Preparation of powder

A powder comprising the following components was prepared in a conventional manner.

Component

Fumarate of 11-(N,N-dimethylaminoethyl)oxy-6,11-dihydrodibenz[b,e]oxepin-2-carboxylic acid ethyl ester (fumarate of compound 11): 30 mg
Lactose: 270 mg

EXAMPLE 23

Preparation of syrup

A syrup comprising the following components was prepared in a conventional manner.

Component

Dihydrochloride of 11-(3-quinuclidinyl)amino-6,11-dihydrodibenz[b,e]oxepin-2-carboxylic acid ethyl ester (dihydrochloride of compound 17): 300 mg
Purified sucrose: 40 g
Methyl p-oxybenzoate: 40 mg
Propyl p-oxybenzoate: 10 mg
Strawberry flavor: 0.1 cc Water was added to the above components until the total volume became 100 cc.

What is claimed is:

1. A dibenz[b,e]oxepin compound of the formula (I):

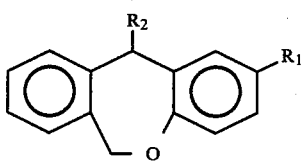

wherein $R_1$ represents a cyano group, a 5-tetrazolyl group, a carbamoyl group or $-CO_2R_3$ wherein $R_3$ represents a hydrogen atom, an alkyl group having 1 to 5 carbon atoms or a 1-(ethoxycarbonyloxy)ethyl group, and $R_2$ represents a 4-alkylpiperazino group wherein the alkyl group has 1 to 5 carbon atoms, a 3-quinuclidinylamino group or $-X-(CH_2)_n-NR_4R_5$ wherein X represents $-NH-$, $-S-$ or $-O-$, $R_4$ and $R_5$ are same or different and each represents an alkyl group having 1 to 5 carbon atoms and n represents 2 or 3; and the pharmaceutically acceptable acid addition salts or metal salts thereof.

2. A compound of claim 1; namely, 11-(4-methylpiperazino)-6,11-dihydrodibenz[b,e]oxepin-2-carboxylic acid dihydrochloride.¼H$_2$O.

3. A compound of claim 1; namely, 11-(N,N-dimethylaminoethyl)thio-6,11-dihydrodibenz[b,e]oxepin-2-carboxylic acid ethyl ester.

4. A compound of claim 1; namely, 11-(N,N-dimethylaminoethyl)thio-6,11-dihydrodibenz[b,e]oxepin-2-carboxylic acid hydrochloride.½H$_2$O.

5. A compound of claim 1; namely, 11-(N,N-dimethylaminoethyl)thio-6,11-dihydrodibenz[b,e]oxepin-2-carbonitrile.

6. A compound of claim 1; namely, 11-(N,N-dimethylaminoethyl)oxy-6,11-dihydrodibenz[b,e]oxepin-2-carboxylic acid ethyl ester.

7. A compound of claim 1; namely, 11-(N,N-dimethylaminoethyl)amino-6,11-dihydrodibenz[b,e]oxepin-2-carboamide.

8. A compound of claim 1; namely, 11-(3-quinuclidinyl)amino-6,11-dihydrodibenz[b,e]oxepin-2-carboxylic acid ethyl ester.

9. A compound of claim 1; namely, 11-(4-methylpiperazino)-6,11-dihydrodibenz[b,e]oxepin-2-carboxylic acid (1-ethoxycarbonyloxy)ethyl ester.

10. A compound of claim 1; namely, 11-(N,N-dimethylaminoethyl)thio-6,11-dihydrodibenz[b,e]oxepin-2-carboxylic acid (1-ethoxycarbonyloxy)ethyl ester.

11. A pharmaceutical composition comprising a pharmaceutical carrier and, as an active ingredient, an effective amount of a dibenz[b,e]oxepin compound defined in claim 1.

12. A pharmaceutical composition according to claim 11, wherein said dibenz[b,e]oxepin compound is 11-(4-methylpiperazino)-6,11-dihydrodibenz[b,e]oxepin-2-carboxylic acid dihydrochloride.¼H$_2$O.

13. A pharmaceutical composition according to claim 11, wherein said dibenz[b,e]oxepin compound is 11-(N,N-dimethylaminoethyl)thio-6,11-dihydrodibenz[b,e]oxepin-2-carboxylic acid ethyl ester.

14. A pharmaceutical composition according to claim 11, wherein said dibenz[b,e]oxepin compound is 11-(N,N-dimethylaminoethyl)thio-6,11-dihydrodibenz[b,e]oxepin-2-carboxylic acid hydrochloride.½H$_2$O.

15. A pharmaceutical composition according to claim 11, wherein said dibenz[b,e]oxepin compound is 11-(N,N-dimethylaminoethyl)thio-6,11-dihydrodibenz[b,e]oxepin-2-carbonitrile.

16. A pharmaceutical composition according to claim 11, wherein said dibenz[b,e]oxepin compound is 11-(N,N-dimethylaminoethyl)oxy-6,11-dihydrodibenz[b,e]oxepin-2-carboxylic acid ethyl ester.

17. A pharmaceutical composition according to claim 11, wherein said dibenz[b,e]oxepin compound is 11-(N,N-dimethylaminoethyl)amino-6,11-dihydrodibenz[b,e]oxepin-2-carboamide.

18. A pharmaceutical composition according to claim 11, wherein said dibenz[b,e]oxepin compound is 11-(3-quinuclidinyl)amino-6,11-dihydrodibenz[b,e]oxepin-2-carboxylic acid ethyl ester.

19. A pharmaceutical composition according to claim 11, wherein said dibenz[b,e]oxepin compound is 11-(4-methylpiperazino)-6,11-dihydrodibenz[b,e]oxepin-2-carboxylic acid (1-ethoxycarbonyloxy)ethyl ester.

20. A pharmaceutical composition according to claim 11, wherein said dibenz[b,e]oxepin compound is 11-(N,N-dimethylaminoethyl)thio-6,11-dihydrodibenz[b,e]oxepin-2-carboxylic acid (1-ethoxycarbonyloxy)ethyl ester.

* * * * *